United States Patent
Sambanthamoorthy et al.

(10) Patent No.: US 11,369,556 B2
(45) Date of Patent: Jun. 28, 2022

(54) ORAL CARE COMPOSITION COMPRISING ROTTLERIN

(71) Applicant: Colgate-Palmolive Company, New York, NY (US)

(72) Inventors: Karthik Sambanthamoorthy, Bridgewater, NJ (US); Harsh Mahendra Trivedi, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/766,766

(22) PCT Filed: Nov. 27, 2017

(86) PCT No.: PCT/US2017/063266
§ 371 (c)(1),
(2) Date: May 26, 2020

(87) PCT Pub. No.: WO2019/103751
PCT Pub. Date: May 31, 2019

(65) Prior Publication Data
US 2021/0000725 A1    Jan. 7, 2021

(51) Int. Cl.
*A61K 8/49* (2006.01)
*A61Q 11/00* (2006.01)

(52) U.S. Cl.
CPC .............. *A61K 8/498* (2013.01); *A61Q 11/00* (2013.01); *A61K 2800/70* (2013.01)

(58) Field of Classification Search
CPC ... A61Q 11/00; A61K 31/7048; A61K 36/185
USPC ............................................. 424/425; 514/27
See application file for complete search history.

(56) References Cited

U.S. PATENT DOCUMENTS

2004/0259816 A1* 12/2004 Pandol ................ A61K 31/198
514/27

FOREIGN PATENT DOCUMENTS

| EP | 2578210 | 4/2013 |
| JP | 2003286144 | 10/2003 |
| JP | 2006104229 | 4/2006 |
| JP | 2014169241 | 9/2014 |

OTHER PUBLICATIONS

Oyedemi et al., "Novel R-plasmid conjugal transfer inhibitory and antibacterial ctivities of phenolic compounds from Mallotus phillippenis (Lam.) Mul.Arg." Journal of Global Antimicrobial Resistance 5 (2016) 15-21. (Year: 2016).*
Gangwar et al., 2014, "Mallotus philippinensis Muell. Arg (Euphorbiaceae): Ethnopharmacology and Phytochemistry Review," BioMed Research International vol. 2014, Article ID 213973, 13 pages.
International Search Report and Written Opinion of the International Searching Authority in International Application No. PCT/US2017/063266, dated Feb. 19, 2018.
Oyedemi et al., 2016, "Novel R-plasmid conjugal transfer inhibitory and antibacterial activities of phenolic compounds from Mallotus philippensis (Lam.) Mull. Arg.," Journal of Global Antimicrobial Resistance 5:15-21.
Patani et al., 2011, "Phytochemical screening of Piper nigrum and Mallotus philipinesis for its antibacterial activity," International Journal of Pharmacy and Technology 3(1):1867-1875.
Perrone et al., 2017, "Resveratrol (3,5,4'-trihydroxystilbene) and its properties in oral diseases," Experimental and Therapeutic Medicine 14(1):3-9.

* cited by examiner

*Primary Examiner* — Walter E Webb

(57) ABSTRACT

An oral care composition including rottlerin in an amount sufficient to reduce a growth of gram-positive bacteria in a mouth treated with the oral care composition.

9 Claims, No Drawings

ORAL CARE COMPOSITION COMPRISING ROTTLERIN

CROSS REFERENCE TO RELATED APPLICATIONS

This application is a United States Application under 35 C.F.R. 371 claiming benefit of PCT Application No. PCT/US2017/063266, filed on Nov. 27, 2017.

BACKGROUND

Dental plaque is a soft, sticky, colorless film of bacteria that forms on the teeth and gums and produces toxins that may inflame or infect gum tissue to cause gingivitis. Gingivitis is the initial stage of gum disease and, if left untreated, may cause periodontitis. In addition, caries or dental decay may also be a product of oral bacteria in the mouth.

Accordingly, it is common to incorporate well-known antimicrobial agents in oral compositions, which destroy or retard the growth of bacteria. The efficacy of conventional antimicrobial agents, however, may be negatively affected by the other ingredients in the oral care product. In addition, recent investigations have found that some of the bacteria present in plaque are exhibiting increased resistance to commonly used antimicrobial agents.

Conventional antimicrobial agents currently used in oral-care consumer products are typically produced from man-made ingredients. For various reasons however, such as lessened environmental impact, allergies, pleasing scent, and personal preference, many consumers prefer products that contain natural or botanically-based active ingredients.

Accordingly, it would be useful to develop oral care compositions, such as toothpastes and mouthwashes, incorporating new antibacterial or antimicrobial agents that inhibit the growth of oral bacteria. Additionally, it would be useful to develop oral care compositions with natural or botanically-based active ingredients.

BRIEF SUMMARY

This summary is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition, including rottlerin in an amount sufficient to reduce a growth of gram-positive bacteria in a mouth treated with the oral care composition.

In another embodiment, the oral care composition includes from 0.01 weight % to 1.0 weight % of an antibacterial agent, based on a total weight of the oral care composition, wherein the antibacterial agent includes rottlerin.

In another embodiment, the oral care composition includes from 0.05 weight % to 1.0 weight % rottlerin.

In another embodiment, the antibacterial agent consists essentially of rottlerin.

In another embodiment, the antibacterial agent includes from 0.10 weight % to 0.75 weight % rottlerin, based on the total weight of the oral care composition.

In another embodiment, the oral care composition lacks another gram-positive antibacterial ingredient other than rottlerin.

In another embodiment, rottlerin is the only gram-positive antibacterial ingredient.

The foregoing and/or other aspects and utilities embodied in the present disclosure may be achieved by providing a method for increasing the antibacterial effect of an oral care composition, including adding an antibacterial agent to the oral care composition, wherein the antibacterial agent includes rottlerin in an amount sufficient to reduce a growth of gram-positive bacteria.

In another embodiment, the oral care composition includes from 0.01 weight % to 1.0 weight % rottlerin.

In another embodiment, the oral care composition includes from 0.05 weight % to 0.75 weight % rottlerin.

In another embodiment, the antibacterial agent consists essentially of rottlerin.

In another embodiment, the antibacterial effect includes decreasing the growth of gram-positive oral bacteria in the mouth of a user of the oral care composition.

The foregoing and/or other aspects and utilities embodied in the present disclosure may also be achieved by using the oral care composition to reduce the growth of oral bacteria.

DETAILED DESCRIPTION

Reference will now be made in detail to the various embodiments in the present disclosure. The embodiments are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the embodiments.

Throughout the specification and claims, the following terms take the meanings explicitly associated herein, unless the context clearly dictates otherwise. Phrases such as "in an embodiment," "in certain embodiments," and "in some embodiments" as used herein do not necessarily refer to the same embodiment(s), though they may. Furthermore, the phrases "in another embodiment" and "in some other embodiments" as used herein do not necessarily refer to a different embodiment, although they may. As described below, various embodiments may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/ B/B/C, A/B/C, etc. In addition, throughout the specification, the meaning of "a," "an," and "the" include plural references. The meaning of "in" includes "in" and "on."

It will also be understood that, although the terms first, second, etc, may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, components, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Unless otherwise specified, all percentages and amounts expressed herein and elsewhere in the specification should be understood to refer to percentages by weight. The amounts given are based on the active weight of the material.

With regard to procedures, methods, techniques, and workflows that are in accordance with some embodiments, some operations in the procedures, methods, techniques, and workflows disclosed herein may be combined and/or the order of some operations may be changed.

*Streptococcus oralis*, *Actinomyces viscosus*, and *Streptococcus mutans* are species of gram-positive bacteria that commonly colonize human mouths. *A. viscosus* is believed to cause periodontal disease and has been found in human dental calculus and root surface caries. Similarly, *S. mutans* and *S. oralis* are also significant contributors to tooth decay and early colonizers of tooth surfaces. *S. mutans* is believed to be one of the initial formers of tooth plaque.

The inventors have unexpectedly and surprisingly discovered a new antibacterial agent, derived from natural sources, that is effective at reducing the growth of gram-positive bacteria. In particular, the inventors have discovered a new antibacterial agent, rottlerin, which is safe and effective at destroying or retarding the growth of bacteria that colonize the oral cavity, such as *S. mutans*, *A. viscosus*, and *S. oralis*.

Formula 1 illustrates a chemical structure of rottlerin, also known as mallotoxin, (5,7-dihydro-2,2-dimethyl-6-(2,4,6-trihydroxy-3-methyl-5-acetylbenzyl)-8-cinnamoyl-1,2-chromene), a small molecule isolated from the pericarps of the plant *Mallotus philippinensis*.

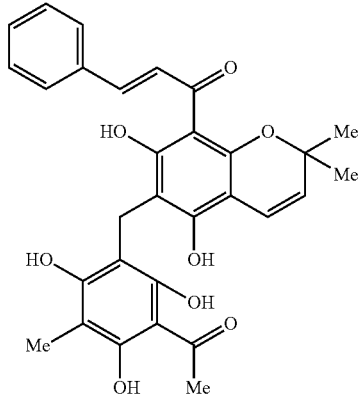

Formula 1

Tables 1-3 illustrate the effects of rottlerin on bacterial growth. In particular, Tables 1-3 illustrate 10-hour bacterial growth in terms of optical density (OD) readings taken at one-hour intervals, where the density readings represent the amount of bacteria present.

The bacterial cultures were grown overnight and standardized to a 0.05 OD reading, after which, different concentrations of rottlerin were added, and the bacterial growth was monitored hourly for 10 hours using a plate reader.

Table 1 illustrates three examples of *S. oralis* bacterial growth: one showing the untreated growth of *S. oralis*, another showing the growth of *S. oralis* after treatment with 10 μM of rottlerin, and a final example showing the growth of *S. oralis* after treatment with 20 μM of rottlerin.

TABLE 1

| Exposure time | 1 hour | 2 hours | 3 hours | 4 hours | 5 hours | 6 hours | 7 hours | 8 hours | 9 hours | 10 hours |
|---|---|---|---|---|---|---|---|---|---|---|
| Untreated *S. oralis* growth (OD) | 0.093 | 0.1 | 0.096 | 0.088 | 0.087 | 0.097 | 0.122 | 0.128 | 0.124 | 0.120 |
| *S. oralis* + 10 μM of rottlerin (OD) | 0.10 | 0.095 | 0.091 | 0.088 | 0.089 | 0.091 | 0.088 | 0.075 | 0.075 | 0.074 |
| *S. oralis* + 20 μM of rottierin (OD) | 0.098 | 0.099 | 0.089 | 0.088 | 0.091 | 0.090 | 0.090 | 0.081 | 0.080 | 0.079 |

Table 2 illustrates three examples of *A. viscosus* bacterial growth: an untreated *A. viscosus* growth, a growth of *A.* viscosus after treatment with 10 μM of rottlerin, and a growth of A. viscosus after treatment with 20 μM of rottlerin.

TABLE 2

| Exposure time | 1 hour | 2 hours | 3 hours | 4 hours | 5 hours | 6 hours | 7 hours | 8 hours | 9 hours | 10 hours |
|---|---|---|---|---|---|---|---|---|---|---|
| Untreated A. viscosus growth (OD) | 0.108 | 0.124 | 0.151 | 0.183 | 0.263 | 0.372 | 0.448 | 0.467 | 0.472 | 0.472 |
| A. viscosus + 10 μM of rottierin (OD) | 0.105 | 0.112 | 0.104 | 0.093 | 0.091 | 0.087 | 0.084 | 0.085 | 0.082 | 0.079 |
| A. viscosus + 20 μM of rottlerin (OD) | 0.105 | 0.122 | 0.121 | 0.115 | 0.113 | 0.106 | 0.1 | 0.097 | 0.091 | 0.086 |

Finally, Table 3 illustrates three examples of mixed species bacterial growth, including equal amounts of S. oralis, S. mutans, and A. viscosus species: an untreated growth, a growth of the mixed species after treatment with 10 μM of rottlerin, and a growth of the mixed species after treatment with 20 μM of rottlerin.

TABLE 3

| Exposure time | 1 hour | 9 hours | 3 hours | 4 hours | 5 hours | 6 hours | 7 hours | 8 hours | 9 hours | 10 hours |
|---|---|---|---|---|---|---|---|---|---|---|
| Untreated mixed species growth (OD) | 0.089 | 0.096 | 0.106 | 0.117 | 0.156 | 0.227 | 0.327 | 0.384 | 0.395 | 0.397 |
| Mixed species + 10 μM of rottierin (OD) | 0.088 | 0.085 | 0.083 | 0.081 | 0.082 | 0.079 | 0.076 | 0.073 | 0.072 | 0.070 |
| mixed species + 20 μM of rottierin (OD) | 0.089 | 0.091 | 0.090 | 0.089 | 0.088 | 0.085 | 0.082 | 0.076 | 0.074 | 0.071 |

As shown in Tables 1-3, the growth of all three strains of bacteria were significantly reduced when exposed to low concentrations of rottlerin as compared to an untreated control.

S. ovalis is a representative streptococcus species of bacteria that colonize the oral cavity and may serve as a representative species for the efficacy of antimicrobial agents. Table 4 (below) illustrates the effects of rottlerin on the metabolic activity and cell viability of S. ovalis when treated with various concentrations of rottlerin. The metabolic activity of the S. ovalis bacteria was measured through ATP assays, and the cell viability was measured using a resazurin assay.

In particular, the cell viability of S. oralis was measured through a resazurin assay as follows: A culture of S. oralis bacteria was grown and standardized to a 610~0.6 OD. 500 μl of the S. oralis bacteria culture was then transferred to a clean and sterile micro-centrifuge tube. The tube was then centrifuged at greater than 15,000 g for 10 minutes to pellet the bacteria. The tube samples were then treated with different amounts of rottlerin and resuspended in 1 ml of 0.25× Trypticase soy broth (TSB) in water. Control and dead samples were created by resuspending the pellet bacteria in sterile media or 100% ethanol, and without adding rottlerin. The tubes were then inverted 3 times for mixing and incubated at 37° C. for 1 hour. Afterwards, 1 ml of D/E neutralizing broth was added to each tube and the samples in the tubes were then washed and stained. The tubes were then centrifuged at greater than 15,000 g for 10 minutes to pellet the bacteria again. The supernate was then removed and the bacteria was resuspended in 1 ml of sterile 0.25× TSB wash. Three 100 μl samples from each tube were then each individually plated in individual wells of a 96-well plate. The samples were then prepared for a standard analytic curve by combining fixed ratios of the live and dead control samples. 100 μl of the resazurin dye solution were then added to each well, and the 96-well plate was then incubated at 37° C. until the live control samples turned the appropriate pink color. A fluorescence plate reader was then used to read the fluorescence of the resazurin dye at 560 nm excitation/590 nm emission, and a percentage of live and dead cells was then calculated.

Similarly, the metabolic activity was measured through an ATP assay as follows: A culture of S. oralis bacteria was grown and standardized to a 610~0.6 OD. 500 μl of the S. ovalis bacteria culture was then transferred to a clean and sterile micro-centrifuge tube and treated as above. Three 100 μl samples from each tube were then individually plated in individual wells of a 96-well plate and 100 μl of Bactitre glow ATP reagent was added. The metabolic activity of the S. oralis bacteria was then monitored by measuring luminescence, with an increase in luminescence correlating with higher metabolic cells.

As shown in Table 4, both the metabolic activity and cell viability of S. oralis was significantly negatively affected (e.g., retarded or reduced) by low concentrations of rottlerin.

TABLE 4

| Rottlerin Amt. | 0.25 μg | 1.25 μg | 2.5 μg | 5 μg | 10 μg | 12.5 μg |
|---|---|---|---|---|---|---|
| Reduction of Metabolic Activity | 40% | 51% | 60% | 61% | 72% | 75% |
| Cell Viability | 79.5% | 61% | 49.4% | 41.1% | 25.9% | 19.9% |

Accordingly, as described in the present disclosure, the inventors have created an oral care composition that includes an antibacterial agent including rottlerin.

In some embodiments, rottlerin is the only antibacterial agent in the oral care composition. In other embodiments, rottlerin is part of a mixture of antibacterial agents in the oral care composition.

In certain embodiments, the oral care composition may include an amount of rottlerin sufficient to inhibit the growth of bacteria in the oral cavity. For example, the oral care composition may inhibit the growth of gram-positive or *streptococcus* bacteria in the oral cavity. In other embodiments, the oral care composition may inhibit the growth of early colonizing bacteria. For example, the oral care composition may include rottlerin in an amount sufficient to reduce the growth of gram-positive or *Streptococcus* bacteria in a mouth treated with the oral care composition. In other examples, the oral care composition may include an amount of rottlerin sufficient to inhibit the growth of at least one of *S. oralis, S. mutans*, and *A. viscosus* in the oral cavity.

In certain embodiments, the oral care composition includes from about 0.01 weight % to about 1.0 weight % rottlerin, based on the total weight of the oral care composition. For example, the oral care composition includes from about 0.05 weight % to about 1.0 weight % rottlerin, from about 0.10 weight % to about 0.75 weight % rottlerin, or from about 0.25 weight % to about 0.50 weight % rottlerin, based on the total weight of the oral care composition. In a preferred embodiment, the oral care composition is embodied as a dentifrice and includes from about 0.01 weight % to about 1.0 weight % rottlerin. In other embodiments, the oral care composition is embodied as a mouthwash and includes about 0.1 weight % or less rottlerin, based on the total weight of the oral care composition. For example, the oral care composition may include from about 0.001 weight % to about 0.1 weight % rottlerin, from about 0.01 weight % to about 0.1 weight % rottlerin, or from about 0.05 weight % to about 0.1 weight % rottlerin.

In some embodiments, the oral care composition may be embodied as a dentifrice and may include additional ingredients common to dentifrice-type oral care compositions, such as carriers, dispersants, whitening agents, flavoring agents, tartar control agents, surfactants, sweeteners, humectants, colorants, antibacterial agents, preservatives, dyes, and pigments.

All ingredients used in the compositions described herein should be orally acceptable. "Orally acceptable" means an ingredient which is present in the composition as described in an amount and form which does not render the composition unsafe, unpalatable, or otherwise unsuitable for use in the oral cavity. In addition, the additional ingredients should not substantially inhibit the efficacy of the antibacterial agent described herein.

The oral care composition may include one or more additional antibacterial agents or preservatives. In some embodiments, the preservatives improve an antimicrobial characteristic of the oral care composition to improve storage life or prevent decay.

In certain embodiments, the one or more antibacterial agents or preservatives include at least one of sodium benzoate, methyl paraben, ethyl paraben, zinc citrate, zinc oxide, triclosan, stannum salts, and combinations thereof.

The oral care composition may include an effective amount of antibacterial agents or preservatives. For example, the oral care composition may include an amount of antibacterial agents or preservatives effective to reduce a spoilage of the oral care composition during storage or use.

In various embodiments of the present disclosure, the oral care composition includes an orally acceptable carrier. As used herein, an "orally acceptable carrier" refers to a material or combination of materials that are safe for use in the oral care compositions of the present disclosure while retaining significant efficacy for the antibacterial agent(s). In certain embodiments, the carrier is specifically selected to ensure that there is no substantially reduction in efficacy for the antibacterial agent(s). For example, the oral care composition may use water as the carrier. In certain embodiments, the oral care composition includes 90 weight % or less, 70 weight % or less, or 50 weight % or less carrier, based on the total weight of the oral care composition.

In certain embodiments, the oral care composition may include one or more humectants. In some embodiments, the humectant is a mixture of humectants, such as glycerin and sorbitol, and a polyhydric alcohol, such as propylene glycol, butylene glycol, hexylene glycol, polyethylene glycol. In certain embodiments, the oral care composition includes from 5 weight % to 40 weight % or from 10 weight % to 30 weight % humectant, based on a total weight of the oral care composition.

The oral care composition may include one or more whitening agent. As used herein, a "whitening agent" is a material that affects whitening of a tooth surface to which it is applied. For example, in some embodiments, the whitening agent is an oxidizing agent. In its broadest sense, "oxidizing agent" is intended to include those compounds which may accept an electron from another molecule in the environment of the oral cavity without having a deleterious or unacceptably harmful effect on the oral cavity in normal and accepted use.

In some embodiments, the whitening agent may include peroxides and hydroperoxides, such as hydrogen peroxide, peroxides of alkali and alkaline earth metals, organic peroxy compounds, peroxy acids, salts thereof, and mixtures thereof. The whitening agent may include peroxides of alkali and alkaline earth metals include lithium peroxide, potassium peroxide, sodium peroxide, magnesium peroxide, calcium peroxide, barium peroxide, and mixtures thereof. The whitening agent may include organic peroxy compounds include urea peroxide, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. The whitening agent may include peroxy acids and their salts include organic peroxy acids such as alkyl peroxy acids, and monoperoxyphthalate and mixtures thereof, as well as inorganic peroxy acid salts such as percarbonate, perphosphate, perborate and persilicate salts of alkali and alkaline earth metals such as lithium, potassium, sodium, magnesium, calcium and barium, and mixtures thereof. In some embodiments a non-peroxide whitening agent may be provided. Whitening agents among those useful herein include non-peroxy compounds include chlorine dioxide, chlorites and hypochlorites. Non-peroxide whitening agents include chlorites and hypochlorites, including those of alkali and alkaline earth metals such as lithium, potassium, sodium, magnesium, calcium and barium. Non-peroxide whitening agents also include colorants, such as titanium dioxide and hydroxyapatite.

In some embodiments, the oral care composition includes from about 0.01% to about 50% whitening agent based on a total weight of the oral care composition. For example, the oral care composition includes from about 0.05 weight % to about 40 weight % whitening agent. In one embodiment, the oral care composition includes about 0.1 weight % whitening agent based on a total weight of the oral care composition.

In one embodiment, the oral care composition includes one or more surfactants. In some embodiments, the surfactants enhance stability of the composition, help clean the oral cavity surfaces through detergency, and provide foam upon agitation, e.g., during brushing with an oral care composition of the disclosure. Surfactants or surface active agents generally achieve increased whitening action by thoroughly dispersing the whitening agent throughout the oral cavity. In various embodiments, suitable surfactants may function as a surface active agent, emulsifier, and/or foam modulator.

Any orally acceptable surfactant, most of which are anionic, nonionic, cationic, or amphoteric, may be used. A combination of surfactants may also be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium cocoyl monoglyceride sulfonate, sodium lauryl sarcosinate, sodium lauryl isoethionate, sodium laureth carboxylate, and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include, without limitation, derivatives of $C_{8-20}$ aliphatic secondary and tertiary amines having an anionic group such as carboxylate, sulfate, sulfonate, phosphate or phosphonate. A suitable example is cocoamidopropyl betaine.

In some embodiments, the oral care composition includes from about 0.01% to about 20.0% surfactant based on a total weight of the oral care composition. For example, the oral care composition includes from about 1.0 weight % to about 10.0 weight % surfactant. In one embodiment, the oral care composition includes about 2 weight % surfactant based on a total weight of the oral care composition. For example, the oral care composition may include about 2 weight % sodium lauryl sulfate.

In certain embodiments, the oral care composition may include thickening agents or thickeners. Any orally acceptable thickening agent may be used, including without limitation carbomers, also known as carboxyvinyl polymers, carrageenans, also known as Irish moss and more particularly carrageenan (iota-carrageenan), high molecular weight polyethylene glycols (such as CARBOWAX™, available from The Dow Chemical Company), cellulosic polymers such as hydroxyethylcellulose, carboxymethylcellulose ("CMC") and salts thereof, e.g., CMC sodium, natural gums such as karaya, xanthan, gum arabic and tragacanth, colloidal magnesium aluminum silicate, and colloidal or fumed silica and mixtures of the same. The thickening agent may be a combination of one or more orally acceptable thickening agents.

In some embodiments, the oral care composition includes from about 0.01% to about 30% thickening agent based on a total weight of the oral care composition. For example, the oral care composition includes from about 0.1 weight % to about 20 weight % thickening agent. In yet another example, the oral care composition includes from about 0.5 weight % to about 10 weight % thickening agent based on a total weight of the oral care composition. For example, the oral care composition may include about 3 weight % fumed silica.

In some embodiments, the oral care composition includes an antioxidant. Acceptable antioxidants include BHA, BHT, vitamin A, vitamin C, carotenoids, vitamin E, flavonoids, polyphenols, ascorbic acid, herbal antioxidants, chlorophyll, melatonin and mixtures thereof. In some embodiments, the oral care composition includes from about 0.001% to about 1% antioxidants based on a total weight of the oral care composition. In one embodiment, the oral care composition includes about 0.03 weight % antioxidant by weight.

In certain embodiments, the oral care composition includes one or more flavoring agents. Useful flavoring agents include any material or mixture of materials operable to enhance the taste of the oral care composition. Any orally acceptable natural or synthetic flavoring agent may be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, x-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methane glycerol acetal (MGA) and mixtures thereof.

In some embodiments, the oral care composition includes from about 0.01% to about 5% flavoring agents based on a total weight of the oral care composition. For example, the oral care composition includes from about 0.05 weight % to about 3 weight % flavoring agents. In yet another example, the oral care composition includes from about 0.1 weight % to about 3 weight %, from about 0.2 weight % to about 2.5 weight %, or about 1.5 weight % flavoring agents based on a total weight of the oral care composition. For example, the oral care composition may include about 1.5 weight % of dental cream flavor.

In some embodiments, the oral care composition may also include one or more sweeteners. Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltital, isomalt, aspartame, neotame, saccharin and salts thereof, sucralose, dipeptide-based intense sweeteners, cyclamates, dihydrochalcones and mixtures thereof. Some embodiments may include one or more sweeteners. In some embodiments, the oral care composition includes from about 0.005% to about 5% sweeteners based on a total weight of the oral care composition. In other embodiments, the oral care composition includes from about 0.01% to about 1% sweeteners based on a total weight of the oral care composition. For example, the oral care composition may include about 0.5 weight % sodium saccharin and about 0.04 weight % sucralose.

In some embodiments, the oral care composition may include colorants. Colorants, such as dyes or pigments, may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants, if included, are present in very small quantities.

In some embodiments, the oral care composition may also include one or more pH modifying agents. The pH modifying agents among those useful herein include acidifying agents to lower pH, basifying agents to raise pH and buffering agents to control pH within a desired range. For example, one or more compounds selected from acidifying, basifying and buffering agents may be included to provide a pH of 2 to 10, or in various embodiments from about 2 to about 8, from about 3 to about 9, from about 4 to about 8, from about 5 to about 7, from about 6 to about 10, and from about 7 to about 9. Any orally acceptable pH modifying agent may be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range. In some embodiments, the oral care composition includes from about 0.01% to about 10% pH modifier agents based on a total weight of the oral care composition. For example, the oral care composition may include about 0.9 weight % sodium acid pyrophosphate (SAPP) and about 2 weight % tetrasodium pyrophosphate (TSPP) as a pH modifier.

The oral care composition of the present disclosure may also include one or more additional active ingredients, which are operable for the prevention or treatment of a condition or disorder of hard or soft tissue of the oral cavity, the prevention or treatment of a physiological disorder or condition, or to provide a cosmetic benefit.

Some embodiments of the present disclosure include a dental abrasive or combination of dental abrasive agents. As used herein, the term "abrasive" or "abrasive agent" also includes materials commonly referred to as "polishing agents." Any orally acceptable abrasive may be used, but typically, type, fineness (particle size) and amount of abrasive should be selected so that tooth enamel is not excessively abraded in normal use of the composition. Suitable abrasives include without limitation silica (in the form of silica gel, hydrated silica or precipitated silica), alumina, insoluble phosphates, calcium carbonate, resinous abrasives such as urea-formaldehyde condensation products and the like.

Among insoluble phosphates useful as abrasives are orthophosphates, polymetaphosphates and pyrophosphates. Illustrative examples are dicalcium orthophosphate dihydrate, calcium pyrophosphate, n-calcium pyrophosphate, tricalcium phosphate, calcium polymetaphosphate and insoluble sodium polymetaphosphate.

Average particle size of an abrasive, if present, is generally from about 0.1 to 100 about μm. For example, in one embodiment, the particle size is from about 1 to about 80 μm or from about 5 to about 60 μm. In some embodiments, one or more abrasives are present in an amount of from about 0.01% to about 70% by weight, based on the total weight of the oral care composition. In other embodiments, the oral care composition includes from about 0.1 weight % to about 60 weight % abrasives. In some embodiments, the abrasive is calcium pyrophosphate. In some embodiments, the oral care composition includes from 0.01 weight % to about 70 weight % calcium pyrophosphate based on a total weight of the oral care composition. In another embodiment, the oral care composition includes about 20 weight % calcium pyrophosphate.

In various embodiments of the present disclosure, the oral care composition includes an anticalculus agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, and diphosphonates. In some embodiments, the anticalculus agent is present in an amount of from about 0.01% to about 30% weight based on the total weight of the oral care composition. In some embodiments, the oral care composition includes a mixture of anticalculus agents. In some embodiments, tetrasodium pyrophosphate (TSPP) and sodium tripolyphosphate (STPP) are used as the anticalculus agents. In some embodiments, the anticalculus agent includes from 0.1% to 10 weight % TSPP, or about 2 weight % TSPP.

The oral care compositions of the present disclosure may also include a synthetic anionic polymeric polycarboxylate. The synthetic anionic polymeric polycarboxylate can act as a stabilizer for the polyphosphate anti-calculus agent and may help to block access of painful or pain-causing materials, such as sugars, to the tooth nerves.

In some embodiments, the oral care composition optionally includes a source of fluoride ions. In some embodiments, the source of fluoride ions is selected from: fluoride, monofluorophosphate (MFP), and fluorosilicate salts. In some embodiments, one or more fluoride ion-releasing compounds are optionally present in an amount providing a total of 100 to 20,000 ppm, 200 to 5,000 ppm, or 500 to 2,500 ppm, fluoride ions. If present, in some embodiments, the amount of fluoride source in the oral care composition ranges from about 0.01% to about 10% by weight, based on the total weight of the oral care composition, typically about 0.5% to about 1.5 weight %. For example, in one embodiment, the oral care composition may include about 0.76 weight % MFP.

The compositions also may include a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. In some embodiments, one or more stannous ion sources are included in the oral care composition. For example, the oral care composition may include from about 0.01% to about 10% stannous ion source by weight, based on the total weight of the oral care composition. In one embodiment, the oral care composition includes from about 0.1 weight % to about 7 weight % stannous ion source or from about 0.2 weight % to about 5 weight % stannous ion source.

EXAMPLES

Aspects of the present disclosure may be further understood by referring to the following examples. The examples are illustrative, and are not intended to be limiting embodiments thereof. Table 5 illustrates a dentifrice composition according to embodiments of the present disclosure. Table 6 illustrates a mouthwash composition according to embodiments of the present disclosure.

TABLE 5

| Ingredients | Dentifrice Composition |
|---|---|
| Rottlerin | 1% |
| Sorbitol | 35% |
| Carrageenan | 0.2% |
| Silica, dicalcium orthophosphate dihydrate | 20% |
| Sodium lauryl sulfate (SLS) | 1.5% |
| Sodium monofluorophosphate, sodium fluoride | 0.24% |
| Tetra sodium pyrophosphate | 2% |
| Zinc citrate | 0.5% |
| Zinc oxide | 1% |
| Triclosan | 0.3% |
| Water and minors | q.s |

TABLE 6

| Ingredients | Mouthwash Composition |
|---|---|
| rottlerin | 0.01% |
| Cetylpyridinium chloride (CPC) | 0.075% |
| glycerin | 23% |
| propylene glycol | 16.07% |
| sorbitol | 23% |
| poloxamer | 0.5% |
| flavor | 0.1% |
| citric acid | 0.2% |
| Sodium saccharin | 0.05 |
| Water and minors | q.s |

The present disclosure has been described with reference to exemplary embodiments. Although a few embodiments have been shown and described, it will be appreciated by those skilled in the art that changes may be made in these embodiments without departing from the principles and spirit of preceding detailed description. It is intended that the present disclosure be construed as including all such modifications and alterations insofar as they come within the scope of the appended claims or the equivalents thereof.

What is claimed is:

1. An oral care composition, comprising rottlerin in an amount sufficient to reduce a growth of gram-positive bacteria in a mouth treated with the oral care composition, wherein the oral composition is a mouthwash comprising from 0.01 weight % to 0.05 weight % rottlerin, based on the total weight of the oral care composition.

2. The oral care composition of claim 1, wherein the antibacterial agent consists essentially of rottlerin.

3. The oral care composition of claim 1, wherein the oral care composition lacks another gram-positive antibacterial ingredient other than rottlerin.

4. The oral care composition of claim 1, wherein rottlerin is the only gram-positive antibacterial ingredient.

5. A method for increasing the antibacterial effect of an oral care composition, comprising:
adding an antibacterial agent to the oral care composition, wherein the antibacterial agent comprises rottlerin; and
wherein the oral care composition is a mouthwash comprising from 0.01 weight % to 0.05 weight % rottlerin, based on the total weight of the oral care composition,
wherein the rottlerin is in an amount sufficient to reduce a growth of gram-positive bacteria.

6. The method of claim 5, wherein the antibacterial agent consists essentially of rottlerin.

7. The method of claim 5, wherein the antibacterial effect comprises decreasing the growth of gram-positive oral bacteria in the mouth of a user of the oral care composition.

8. The oral care composition of claim 1, wherein the gram-positive bacteria is selected from: *S. oralis, S. mutans, A. viscosus* and combinations thereof.

9. The method of claim 7, wherein the gram-positive oral bacteria is selected from: *S. oralis, S. mutans, A. viscosus* and combinations thereof.

* * * * *